United States Patent [19]

Newell et al.

[11] Patent Number: 4,678,106
[45] Date of Patent: Jul. 7, 1987

[54] DISPENSING DEVICE

[75] Inventors: Robert E. Newell, Pinner; Paul K. Rand, Hitchin; Carole A. Osterweil, London, all of England

[73] Assignee: Glaxo Group Limited, London, England

[21] Appl. No.: 760,596

[22] Filed: Jul. 30, 1985

[30] Foreign Application Priority Data

Jul. 31, 1984 [GB] United Kingdom ............... 8419437

[51] Int. Cl.⁴ .......................................... B67D 5/64
[52] U.S. Cl. .................................. 222/162; 222/182; 222/183; 222/402.15; 222/402.11
[58] Field of Search ............... 222/162, 181, 182, 183, 222/402.13, 402.11, 402.15

[56] References Cited

U.S. PATENT DOCUMENTS

| 3,405,843 | 10/1968 | Watson, Jr. ............... 222/162 X |
| 3,789,843 | 2/1974 | Armstrong ................. 128/200.23 |
| 4,079,862 | 3/1978 | Fegley ...................... 222/162 |
| 4,324,348 | 4/1982 | Johnson et al. ............ 222/181 |
| 4,402,430 | 9/1983 | Fox et al. .................. 222/183 |

FOREIGN PATENT DOCUMENTS

| 0089070 | 9/1983 | European Pat. Off. . |
| 0147028 | 7/1985 | European Pat. Off. . |
| 104194 | 3/1974 | German Democratic Rep. . |
| 1335378 | 10/1973 | United Kingdom . |

Primary Examiner—L. J. Paperner
Assistant Examiner—Jay I. Alexander
Attorney, Agent, or Firm—McAulay, Fields, Fisher, Goldstein & Nissen

[57] ABSTRACT

A device is provided for dispensing a mixture of propellant and product (e.g. medicament) from a pressurized aerosol container (3). The device has a housing (1) receiving the container (3), a cover (7) and an actuator lever (10) all pivotally connected to one another. The axes of pivoting are so arranged that moving the cover (7) from a closed position to an open position puts the device in a "primed" condition in which squeezing the housing (1) and actuator lever (10) together displaces the container (3) with respect to the housing (1) and thereby opens the outlet valve (4) of the container (3) to dispense mixture from the container.

7 Claims, 4 Drawing Figures

DISPENSING DEVICE

BACKGROUND OF THE INVENTION

This invention relates to a device for dispensing a mixture of propellant and product from a pressurised aerosol container. In a preferred application the product is a medicament.

Aerosols containing a mixture of medicament and propellant are commonly used, for example in treating conditions of the upper and lower respiratory tract. For treating such conditions medicaments are dispensed in spray form to a patient by means of an oral or nasal inhalation device comprising a housing or sleeve in which a pressurised aerosol container is located and a mouthpiece or nozzle leads out of the tubular housing. In use, the aerosol container is placed in the housing which is then held by the patient in a more or less upright condition and the mouthpiece or nozzle of the inhalation device is placed in the mouth or nostril of the patient. The patient inhales while operating the aerosol container to open the outlet valve of the container and to dispense medicament from the container through the mouthpiece or nozzle into the mouth or nostril of the patient.

With all such devices, the patient dispenses medicament by pressing on a portion of the aerosol container which protrudes from the housing. When such pressure is exerted, the aerosol container is displaced with respect to the housing thereby to open the outlet valve of the aerosol container. Some patients, for example children, geriatrics, arthritics and the infirm, have difficulty in holding the inhalation device to the mouth or nostril whilst depressing the aerosol container with respect to the housing in order to open the outlet valve. Others have difficulty in coordinating movements of their hands with inhalation and as a result may fail to take the desired dosage of medicament.

It is an object of the present invention to provide a way of making it easier for such patients to dispense medicament from an aerosol container and also to provide a way of substantially enclosing the aerosol container, aerosol housing and mouthpiece or nozzle when the device is not in use.

SUMMARY OF THE INVENTION

A device for dispensing a mixture of propellant and product from a pressurised aerosol container having an outlet valve, comprises a housing receiving, or adapted to receive, a pressurised aerosol container and having an outlet spout near one end thereof; a cover having a pivotal connection to the housing near the other end of the housing, the cover being movable from a closed position in which it encloses the outlet spout to an open position in which the outlet spout is exposed; and an actuator lever arranged for pivotal movement with respect to the housing so that it may be closed on to a portion of the housing not covered by the cover and having a portion which when, and only when, the cover is in its open position and the lever is closed on to the housing exerts a force on the container to displace the container with respect to the housing and thereby opens the outlet valve of the container to dispense the said mixture from the container through the outlet spout.

The outlet spout may be constructed as a mouthpiece to be placed in the mouth of a patient or it may be constructed as a nozzle for insertion into the nostril of a patient.

In preferred embodiments, the cover is hinged to the body and the actuator lever is hinged to the cover.

DESCRIPTION OF PREFERRED EMBODIMENTS

Figure 1:
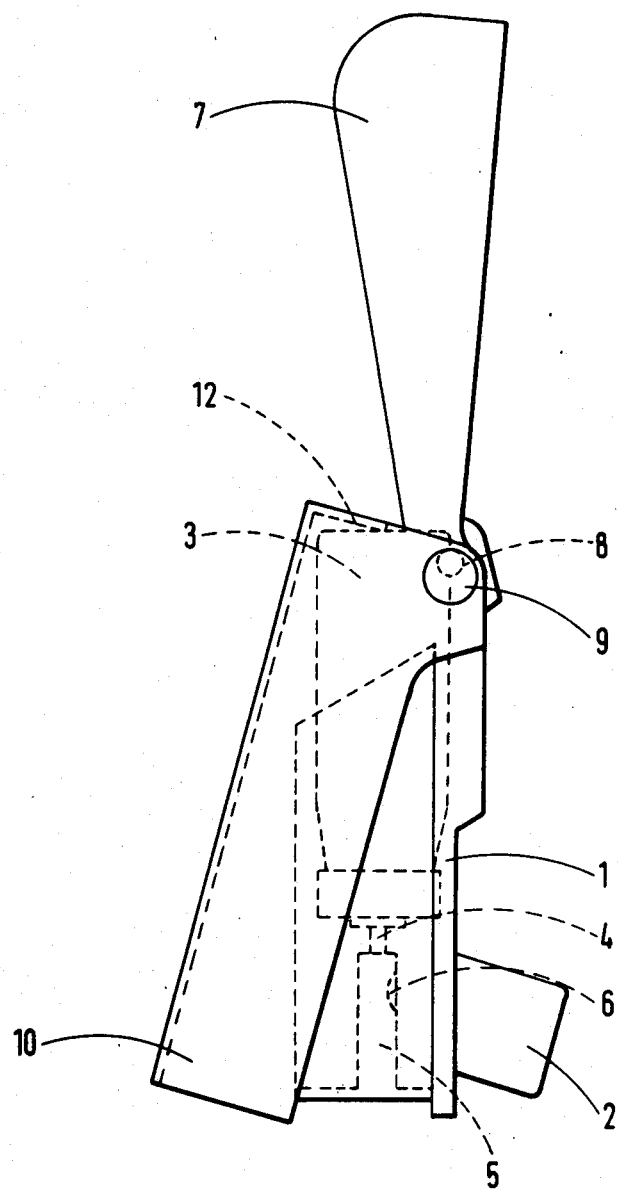
FIG. 1 is an elevation of inhalation device according to one embodiment of the invention, showing a cover thereof in an open position and the device in a primed position.
Figure 2:
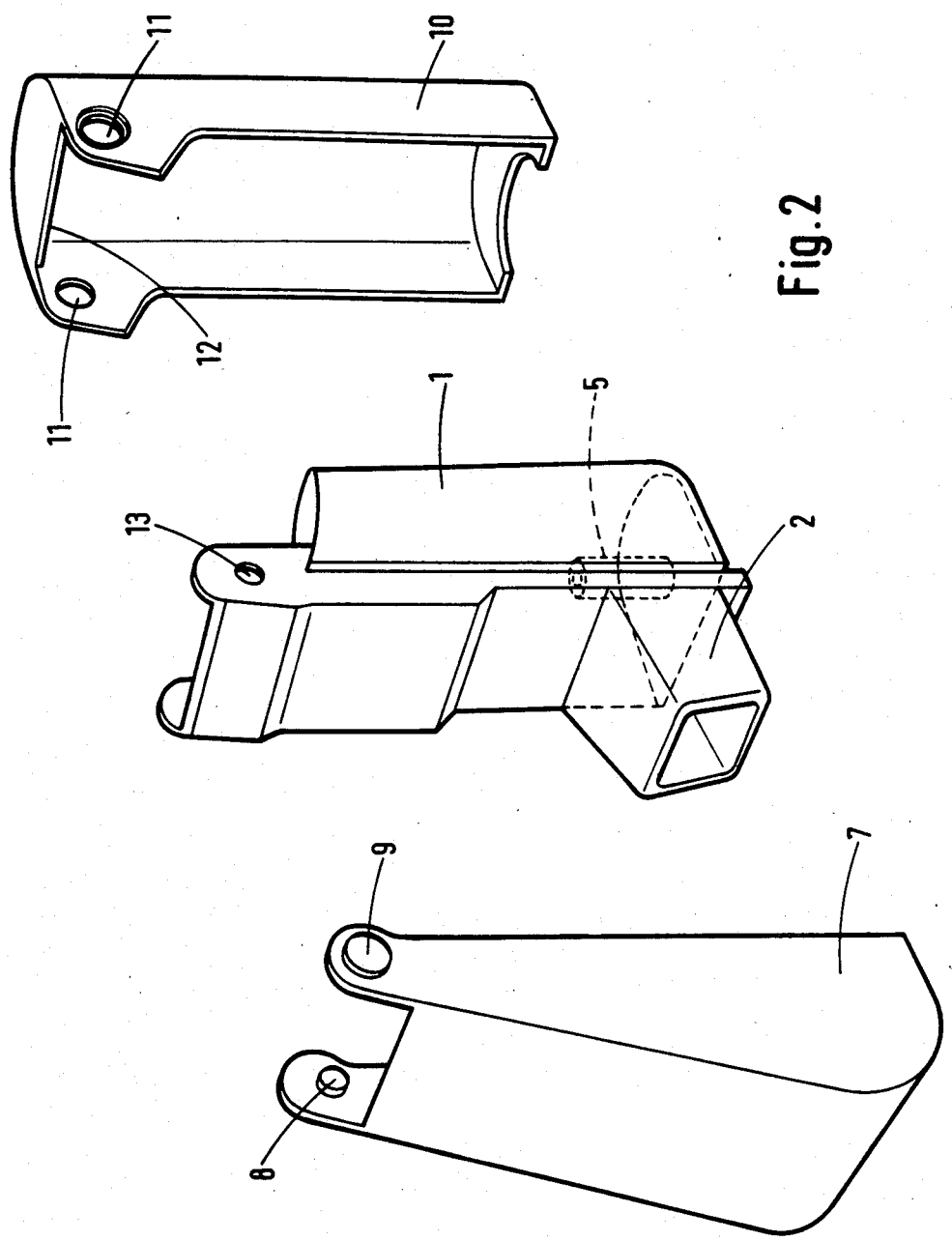
FIG. 2 is an exploded perspective view of the device of FIG. 1.

In the embodiment illustrated in FIGS. 1 and 2, an inhalation device for medicaments contained in an aerosol cannister comprises a hollow body 1 which is open at one end, herein considered to be the top end of the body for convenience of description. When the device is in use, the body is normally held by a patient in this position. The body has an outlet spout 2 protruding laterally from near the other, i.e. lower end of the body. A pressurised aerosol cannister 3 (FIG. 1) may be placed in the body 1 in an inverted condition as shown in FIG. 1. An outlet valve member 4 of the cannister 3 is engaged with a stem block 5 at the bottom of the body 1. The stem block 5 has an outlet passage 6 (FIG. 1). When the cannister 3 is pressed down with respect to the stem block 5, the valve member 4 will, of course, remain stationary since it is engaged with the stem block, and the relative movement between the aerosol cannister and the valve member will open the valve member 4, so that a dose of the medicament and propellant mixture will be discharged from the cannister 3, pass through the passage 6 and enter the mouth of the patient through the outlet spout 2.

A cover 7 is hingedly connected near the open top of the body 1. For this purpose, the cover 7 has near it upper end internal pins 8 which engage in holes 13 in the body. Because of this hinged connection, the cover 7 can be moved between a closed position in which its lower end portion encloses the outlet spout 2 and an open position in which the outlet spout is exposed. In use, the cover is swung through approximately 180° to the position shown in FIG. 1. The cover 7 has two external pins 9 the centres of which are offset relative to the centres of the pins 8. An actuator lever 10 has near its upper end holes 11 in which the pins 9 are received so that the lever is hingedly connected to the body through the cover. This lever 10 fits round a portion of the body 1 not covered by the cover 7. In certain positions the underside of the lever roof 12 will act as a fulcrum against the aerosol container 3. It is preferred that the pins 8 have a diameter which is approximately one half of the diameter of the external pins 9. The pin 8 is arranged to move with an epicycloidal motion when the cover is raised to prime the device and, when the lever is depressed, to fire the device. Alternatively (not shown), the pin 8 could be arranged to move with a hypocycloidal motion.

To prime the device ready for use, the patient opens the cover 7, preferably to the fully open position illustrated in FIG. 1. The relative motion of the pins 8 and 9 moves the aerosol container 3 and the body 1 in an upwards direction relative to the lever 10 to a position where the aerosol container contacts the underside of a lever roof 12 and continued movement of the cover 7 causes the lever 10 to pivot upwards and outwards to a "primed position" (FIG. 1).

To use the device, the patient inserts the outlet spout 2 into his mouth and fires the aerosol by compressing the body 1 and the lever 10 together. During compression the underside of the lever roof 12 exerts pressure on the aerosol container 3, causing the valve member 4 to discharge a dose through the outlet passage 6 and the outlet spout 2 into the mouth of the patient.

If required, the patient can take further doses by compressing the body and lever repeatedly together, or he can close the device by lowering the cover 7 over the outlet spout 2.

Figure 4:
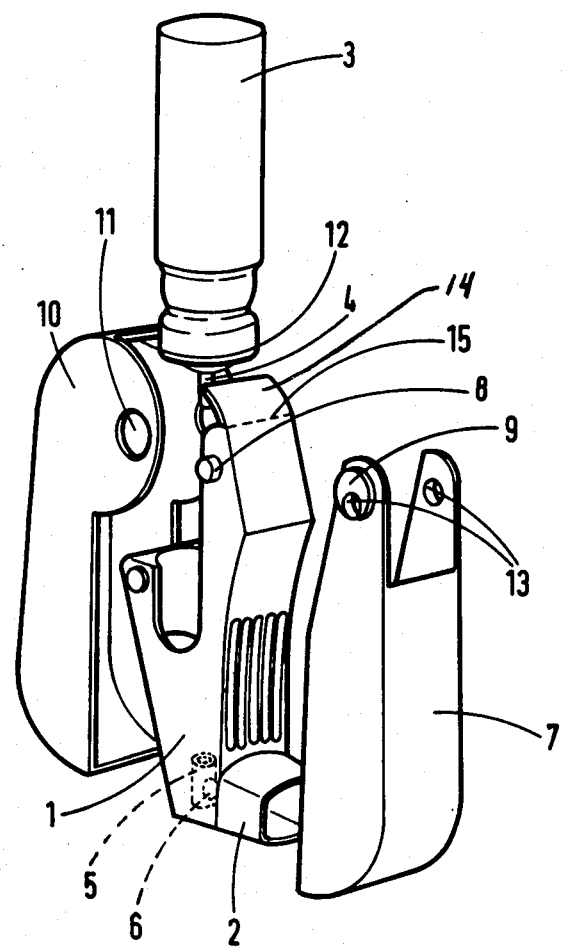
FIG. 4 is an exploded perspective view of the device of FIG. 3.
Figure 3:
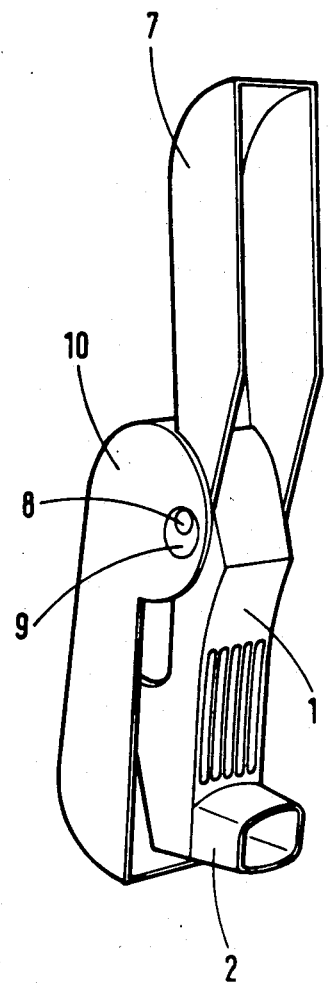
FIG. 3 is a view corresponding to FIG. 1 but showing a second embodiment.

The second embodiment, shown in FIGS. 3 and 4, is broadly similar in construction and operation to that shown in FIGS. 1 and 2 and will therefore not be described in detail. In FIGS. 3 and 4 the same reference numerals are used as in FIGS. 1 and 2 for the corresponding parts. Attention is, however, directed to a number of differences from the first embodiment. Firstly, the arrangement of the pins 8 and 9 and the holes 11 and 13 is different. The pins 8 are formed on the outside of the body 1 (instead of the inside of the cover 7) and the holes 13 are formed eccentrically through the pins 9 on the cover 7 (instead of through the body 1). Geometrically, the effect is the same as that achieved by the first embodiment, but the second embodiment has the advantage of being easier to manufacture. Secondly, the end of the aerosol cannister remote from the outlet spout is covered to a greater extent than in the first embodiment by the provision of flap 14 pivotally connected to the rest of the body 1 by an integral plastics hinge the position of which is denoted by a broken line 15. The flap extends partly under the lever roof 12.

Although in both the embodiments described above the cannister 3 is removable from the device to enable a fresh cannister to be inserted, the device could be intended for disposal after a single cannister had been exhausted, in which case the cannister could be inserted during manufacture and need not be removable thereafter.

We claim:

1. A device for dispensing a mixture of propellant and product from a pressurized aerosol container having an outlet valve, comprising a housing receiving, or adapted to receive, a pressurized aerosol container, the housing having an outlet spout near one end thereof; a cover; cooperating pivot means on the cover and on the housing near the other end thereof, which provide for pivotal movement between the cover and the housing about a first axis, the cover being pivotal from a closed position in which it encloses the outlet spout to an open position in which the outlet spout is exposed; an actuator lever having a portion disposed to be engagable with the container to exert an axial force thereon; cooperating pivot means on the cover and the lever which provide for pivotal movement between the cover and the lever, the lever being pivotally closable onto a portion of the housing not covered by the cover, pivotal movement between the cover and lever being about a second axis which is parallel to said first axis and is spaced therefrom, whereby movement of the cover from its closed position to its open position shifts the position of said first axis with respect to said second axis, said shift being such as to bring said container-engaging portion of said lever into engagement with said cover so that when the lever is closed on the housing it exerts a force on the container to displace the container with respect to the housing and to open the outlet valve of the container to dispense said mixture from the container through the outlet spout.

2. A device according to claim 1, wherein the cover carries two pairs of pivot pins, a smaller pair received in a corresponding pair of apertures in the housing for defining said first axis of pivotal movement, and a larger pair received in a corresponding pair of apertures in the actuator lever for defining said second axis of pivotal movement.

3. A device according to claim 1, wherein the cover carries a first pair of pivot pins received in a corresponding pair of apertures in the actuator lever, and the housing carries a second pair of pivot pins, smaller than the first pair, received in a corresponding pair of apertures formed in the cover in the region of the first pair of pivot pins.

4. A device according to claim 2, wherein the smaller pair of pivot pins have a diameter approximately half that of the larger pair.

5. A device according to claim 3, wherein the second pair of pivot pins have a diameter approximately half that of the first pair.

6. A device according to claim 1, wherein a stem block is provided in the housing for receiving the outlet valve of the container removably therein.

7. A device according to claim 1, wherein said container-engaging portion of the lever is constituted by a roof portion of the lever.

* * * * *